(12) United States Patent
Tepic

(10) Patent No.: US 10,792,139 B2
(45) Date of Patent: Oct. 6, 2020

(54) TREATMENT OF KNEE DISORDERS IN THE DOG

(71) Applicant: Kyon AG, Zurich (CH)

(72) Inventor: Slobodan Tepic, Zurich (CH)

(73) Assignee: Kyon AG, Zurich (CH)

( * ) Notice: Subject to any disclaimer, the term of this patent is extended or adjusted under 35 U.S.C. 154(b) by 0 days.

(21) Appl. No.: 15/690,611

(22) Filed: Aug. 30, 2017

(65) Prior Publication Data

US 2019/0060043 A1 Feb. 28, 2019

(51) Int. Cl.
| | | |
|---|---|---|
| *A61F 2/08* | (2006.01) | |
| *A61D 1/00* | (2006.01) | |
| *A61B 17/16* | (2006.01) | |
| *A61B 17/06* | (2006.01) | |
| *A61B 17/3209* | (2006.01) | |
| *A61B 17/56* | (2006.01) | |

(52) U.S. Cl.
CPC .......... *A61D 1/00* (2013.01); *A61B 17/06166* (2013.01); *A61B 17/1675* (2013.01); *A61B 17/3209* (2013.01); *A61F 2/08* (2013.01); *A61B 2017/564* (2013.01); *A61B 2503/40* (2013.01); *A61F 2250/0081* (2013.01)

(58) Field of Classification Search
CPC . A61F 2/08; A61F 2250/0081; A61B 2503/40
See application file for complete search history.

(56) References Cited

U.S. PATENT DOCUMENTS

2010/0010549 A1* 1/2010 Alleyne ................... A61F 2/08
  606/86 R
2018/0125550 A1* 5/2018 Shenoy ............. A61B 17/8061

OTHER PUBLICATIONS

Monnet et al, Popliteal tendon transposition for stabilization of the cranial cruciate ligament deficient stifle joint in dogs: an experimental study (Year: 1995).*
Slocum B, Slocum TD, Tibial Plateau Leveling Osteotomy for Repair of Cranial Cruciate Ligament Rupture in the Canine, Vet. Clin. North Am. 23: 777-795, 1993.
Slocum B, Devine T, Cranial Tibial Wedge Osteotomy: A Technique for Eliminating Cranial Tibial Thrust in Cranial Cruciate Ligament Repair, J. Am. Vet. Med. Assoc. 184: 564-569, 1984.
Tepic S, Damur DM, Montavon PM, Biomechanics of the Stifle Joint, in Proceedings of the 1st World Orthopaedic Vet. Congress, Munich, Germany, Sep. 2002, pp. 189-190).
Boudrieau RJ, Tibial plateau leveling osteotomy or tibial tuberosity advancement? Vet Surg. Jan. 2009; 38(1):1-22.

(Continued)

*Primary Examiner* — Bruce E Snow
(74) *Attorney, Agent, or Firm* — Occhiuti & Rohlicek LLP

(57) ABSTRACT

The present invention provides a surgical treatment for a disordered knee in a dog, the disorder comprising a partially ruptured cranial cruciate ligament (CrCL), a fully ruptured CrCL, or a displaced patella. The methods of treatment include surgical transection of the tendon of the popliteal muscle, which reduces the in-toeing of the paw as it lands on the ground. In vitro experiments suggest that neutralization of this torque can reduce by several fold tensile forces in the CrCL or its replacement, as well as in its surrogate, a lateral suture placed extra-capsularly.

23 Claims, 3 Drawing Sheets

(56) References Cited

OTHER PUBLICATIONS

Wilke VL, Robinson DA, Evans RB, Rothschild MF, Conzemius MG, Estimate of the annual economic impact of treatment of cranial cruciate ligament injury in dogs in the United States, J Am Vet Med Assoc. Nov. 15, 2005;227 (10)1604-7.

Amoczky SP, Marshall JL, The cruciate ligaments of the canine stifle: an anatomical and functional analysis, Am J Vet Res. Nov. 1977; 38(11):1807-14).

Sumner JP, Markel MD and Muir P, Caudal Cruciate Ligament Damage in Dogs with Cranial Cruciate Ligament Rupture, Veterinary Surgery, 39: 936-941, 2010.

Miller's Anatomy of the Dog, third edition, W.B. Saunders Company, 1993, p. 373p.

K.M. Tobias and S.A. Johnston, Veterinary Surgery, Small Animal, vol. 1, Elsevier Saunders, 2012, p. 930-931.

\* cited by examiner

US 10,792,139 B2

TREATMENT OF KNEE DISORDERS IN THE DOG

FIELD OF THE INVENTION

The present invention relates to methods useful in treating disorders of the knee, termed the stifle in dogs, including surgical methods in which the tendon of the popliteal muscle is transected.

BACKGROUND OF THE INVENTION

The anterior cruciate ligament (ACL) in the human knee joint, commonly called the cranial cruciate ligament (CrCL) in the canine stifle, is frequently torn in trauma. It also frequently fails, particularly in dogs, after a degenerative process of still unknown etiology.

In human orthopedics, standard procedures replace the failed ACL with an ACL allograft made from a part of the patient's own patellar tendon or a part of the fascia and tendon removed from the hamstring muscles. The procedure results in a stable knee, but the long-term performance of the knee is often unsatisfactory. Roughly 75-90% of cases result in degenerative arthritis of the joint within 15 years of the procedure.

In dogs, the standard procedure involves either placement of an extra-capsular suture or performance of one of several geometry-modifying surgical techniques. In the extra-capsular procedure, a suture is placed outside of the joint, usually on the lateral side, to approximate the function of the CrCL. The intention of the suture application is to provide stability of the joint for several weeks while waiting for fibrosis to occur around the joint. This fibrosis should then provide for long-term stability. However, the extra-capsular suture technique regularly results in failure. Degenerative arthritis of the joint, after a year or so, is the rule rather than the exception.

Attempts to replace the CrCL in the dog by an anatomically placed, intra-articular artificial ligament have also generally failed in spite of years of research and development of materials, anchor designs, and surgical techniques.

In surgical, geometry-modifying techniques, the tibia is cut and a segment of it is repositioned to change the geometry of the tibia and/or the joint in order to stabilize the stifle. Various techniques have been used, including: tibial plateau leveling osteotomy (TPLO; see U.S. Pat. No. 4,677,973 and Slocum and Slocum, *Vet. Clin. North Am.* 23:777-795, 1993), cranial closing wedge osteotomy (CWO; Slocum and Devine, *J. Am. Vet. Med. Assoc.* 184:564-569, 1984), and tibial tuberosity advancement (TTA; Tepic et al., *Biomechanics Of The Stifle Joint*, in Proceedings of the 1st World Orthopaedic Veterinary Congress, Munich, Germany, pp. 189-190. 2002). Of the surgical approaches used in dogs, TTA seems to be associated with less morbidity and faster recovery, and it also provides immediate and durable stability to the joint (Boudrieau, *Vet Surg.*, 38(1): 1-22, 2009). Nevertheless, surgical complications are not uncommon with all these techniques. The most common is post-surgical damage to the medial meniscus caused by excessive, supra-physiological movement between the femur and the tibia.

SUMMARY OF THE INVENTION

The present invention provides methods for surgically treating a disordered knee in a dog by surgically transecting the tendon of the popliteal muscle. The disorder can be a partial or complete rupture of the cranial cruciate ligament (CrCL) due to any circumstance (e.g., due to trauma or a disease process), and the methods of the invention can also be applied to treat a medially luxating patella. The methods of invention emerged from our study of the probable origin of cruciate disease in the dog and our efforts to rectify the problem of external loading that induces torque in the stifle and consequently very high tensile forces in the cruciate ligaments as they wrap around each other to limit internal rotation of the tibia, particularly at the very beginning of the stance phase. Surgical transection of the tendon of the popliteal muscle eliminates the in toeing of the paw as it lands on the ground. Our in vitro observations suggested that neutralizing this torque could reduce tensile forces by several fold in the cranial cruciate ligament or its replacement, as well as in its surrogate, a lateral suture placed extra-capsularly. The transection of the tendon of the popliteal muscle can be performed as a sole intervention in, for example, partial ruptures of the cruciate ligaments or in patellar luxations (particularly during the earlier stages). It can also be performed as an adjunct procedure in, for example, extra-capsular or intra-articular suture implantations.

Accordingly, the present invention features methods of treating a disordered dog stifle by surgically transecting the tendon of the popliteal muscle. As noted, the stifle may include a partially or fully ruptured cruciate ligament (e.g., the CrCL and/or the caudal cruciate ligament), which we may refer to as cranial cruciate ligament disease (CrCLD). Disorders of the dog stifle also amenable to treatment are dislocations of the patella (e.g., a medially luxating patella).

DETAILED DESCRIPTION

Figure 1:
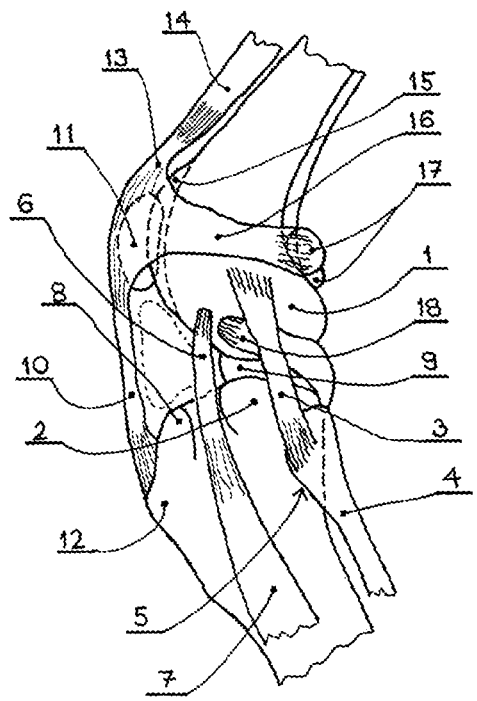
FIG. 1 is a lateral view of the main ligaments and tendons of the canine stifle (left leg).

This invention is based, at least in part, on in vitro experiments and clinical observations that have helped us identify the fundamental causes of the slow process of degradation of the CrCL in the dog. Our experimental work with dog cadavers has shown a surprisingly strong effect of the torque imposed on the stifle by the ground reaction at the paw on the tensile force in the CrCL, as well as on its surrogate, a lateral extra-capsular suture. Compared to the loading confined to the sagittal plane, where the effect of the slope is measured directly and exclusively, the tension on the CrCL and its extra-capsular surrogate was increased greatly—by up to six times—if the torsion was accounted for by applying the load to the paw. In an intact stifle, when the muscle forces fail to provide perfect balance of internal and external rotators to offset externally applied loads, the cruciate ligaments wrapping around each other provide the limit to internal rotation (Arnoczky and Marshall, *Am. J. Vet. Res.* 38(11):1807-1814, 1977). This causes very high tensile forces in the ligaments. It has been shown by observation that in nine out of ten cases of failed CrCL repair, the caudal cruciate ligament is also damaged (Sumner et al., *Veterinary Surgery*, 39:936-941, 2010). In one out of four cases in this study there was a full thickness defect of the caudal ligament. Interestingly, all geometry-modifying surgeries increase the load on the remaining caudal cruciate ligament, yet post-intervention failures are extremely rare. The explanation for this surprising observation is that in the absence of the CrCL, the tension creating wrapping of the two ligaments is gone. Periarticular tissues then take on the role of limiting the internal rotation, even if with less well-defined range and robustness.

Other than major deformities of the limb bones, which is absent in most clinical cases of CrCLD, the major functional driver of torque-generating internal rotation is the popliteal muscle, which is the most highly specialized muscle acting to internally rotate the tibia (*Miller's Anatomy of the Dog*, Third Edition, W.B. Saunders Company, 1993, pg. 373). There is only sparse information available about its function in dogs, but it seems to fire mostly during the swing phase of the gait. If so, it would define the position of the paw as it lands on the ground, thus setting up pre-conditions for the torque-induced tension in the cruciate ligaments as they wrap on each other. The only plausible remedy would be perfectly timed and balanced action of the biceps femoris muscle, which is the only major external rotator of the tibia. However, all of the stifle spanning muscles inserting to the medial side of the proximal tibia are not only flexors, involved in controlling the stifle angle in the sagittal plane together with the quadriceps that act as stifle extensors, but also internal rotators of the tibia. The task of the biceps femoris is further complicated because it also functions as a stifle flexor.

Following these intricate relationships of the muscles controlling the relative rotation at the stifle around two axes, and the extremely high tensile loads that can be developed by internal rotation of the tibia, the inventor surmised that the primary cause of CrCLD in dogs is undercompensated internal rotation of the tibia that stresses the cruciate ligaments.

A rational surgical intervention to be used in conjunction with cranial cruciate repair or replacement by a surrogate ligament are methods of releasing the tendon of the popliteal muscle as described herein (e.g., at or near its origin). The origin of the popliteal muscle tendon is on the distal lateral side of the femoral condyle, just beneath the lateral collateral ligament. It is in the surgical access field for placement of the lateral suture and can be transected with minimal morbidity. Transection of the tendon at or near the origin nullifies the action of the popliteal muscle during the swing phase and leads to placement of the paw more laterally, reducing or eliminating the external torque that drives the tibia into internal rotation.

As suggested by the aforementioned in vitro experiments, this can lead to a several fold reduction of the tension in the implants aiming to restore the function of the cranial cruciate ligament, both of intra-articular and extra-articular type.

As for the possible unwanted side effects of this intervention, we can find some comfort in the fact that the insertion of the popliteal muscle on the tibia is exposed to major disruption, if not a complete release, to allow for packing of some gauze between the bone and the soft tissues as a protection from potential damage with the TPLO oscillating saw. This part of the TPLO procedure has been granted very little attention, suggesting the absence of any major issues due to incidental disruption in the function of this muscle. To prevent eventual healing of the transected tendon and restoration of the unwanted function, the distal end of the transected tendon can be sutured or otherwise affixed to another structure (e.g., the proximal tibia), rendering the intervention essentially permanent.

Another very common orthopedic problem in dogs is medial luxation of the patella. A straightforward analysis by inspection suggests that this malfunction can have the same origin—external torque caused by the paw placement medially at the start of the loaded gait phase (referred to as in-toeing in human gait). Due to similarities in cause, the remedy can be the same as described herein for CrCLD—transection of the popliteal tendon at or near its origin. If this is done in the earlier stages of patellar luxation, no further intervention may be needed. Surgical standard of care today involves tibial tuberosity transposition and deepening of the patellar groove. These procedures are more likely to result in complications and have a much higher morbidity than transection of the tendon as described herein.

As noted above, the surgical methods described herein can be applied where there is a partial rupture of the CrCL in dogs. TPLO and TTA geometry modifying procedures are currently performed for both total and partial ruptures of the ligament with about 30% of all cases being partial ruptures. Clinical signs are present and the experience suggests that most of the partial ruptures will progress to total ruptures. Performing the surgery at this earlier stage may have an important advantage in that meniscal damage is much less likely to develop until the complete rupture. Some surgeons will remove the remnants of the partially torn ligament at the time of performing TPLO or TTA, but others will leave it. There are some indications that a partially ruptured ligament will not progress to a full rupture and may even partially heal.

If the transection of the tendon of the popliteal muscle is performed in cases of partial CrCL rupture, the prospects are good that a further, much more invasive procedure, such as TPLO or TTA, will not be necessary. The cruciate ligaments may not keep wrapping on each other to limit the internal rotation of the tibia and may instead go on to heal.

As noted herein, in some situations, transection of the tendon of the popliteal muscle may be deployed alone and can alone resolve the clinical problem, while in other situations, transection is performed as an adjunct intervention to improve the prospects of conventional surgeries. Accordingly, in some embodiments of the present methods, transecting the tendon is the sole intervention performed to treat the disordered dog stifle. In other embodiments, the surgical methods include transecting the tendon and performing a conventional treatment for treating the disordered dog stifle. The conventional treatment can include, for example, placing an extracapsular lateral suture, replacing an intraarticular cranial cruciate ligament, performing a tibial plateau leveling osteotomy (TPLO), and/or performing a tibial tuberosity advancement (TTA) procedure.

Following a standard lateral approach to the stifle (Tobias and Johnston, *Veterinary Surgery, Small Animal*, Vol. 1, Elsevier Saunders, pp. 930, 2012) used for placement of an extra-capsular lateral suture, one can identify the main ligaments and tendons as shown in FIG. 1. The lateral condyle of the femur 1 articulates with the lateral condyle of the tibia 2. Both are of convex shape and thus prone to luxation without ligaments that span the joint connecting the two bones. The lateral collateral ligament 3 originates at the femoral condyle 1 and inserts distally to the head of the fibula 4. The fibula is connected to the tibia at the tibiofibular joint 5. The tendon 6 of the long digital extensor muscle 7 originates at the very distal lateral aspect of the lateral femoral condyle, gliding in the sulcus just caudal to the tuber of Gerdy 8 (there is no consensus on the use of this name borrowed from human anatomy). Lateral meniscus 9 resides between the condyles 1 and 2. The main complication of all procedures to treat a ruptured CrCL is post-treatment damage to menisci, more commonly to the medial one. Damage to the menisci, which are crucial in providing a seal for the fluid trapped in the cartilage layers covering the condyles, leads to a rapid progression of degenerative arthritis.

The patellar tendon 10 originates at the patella 11 and inserts at the proximal, cranial aspect of the tibial tuberosity 12. Insertion of the tendons 13 of the quad muscles 14 at the proximal aspect of the patella completes the tensile extensor mechanism of the stifle. The patella is a sesamoid bone, in which case, by some accounts, the distal tendon of the quad muscles and the patellar tendon are parts of the same tendon. The patella 11 is secured in its groove 15, by the medial and lateral femoropatellar ligaments 16 attaching on both sides of the joint to the respective fabellae 17.

Adjacent to and between the origins of the lateral collateral ligament and the tendon of the long digital extensor is the origin of the tendon 18 of the popliteal muscle. The tendon 18 of the popliteal muscle passes under the lateral collateral ligament 3 and wraps around the caudal aspect of the stifle.

Figure 2:
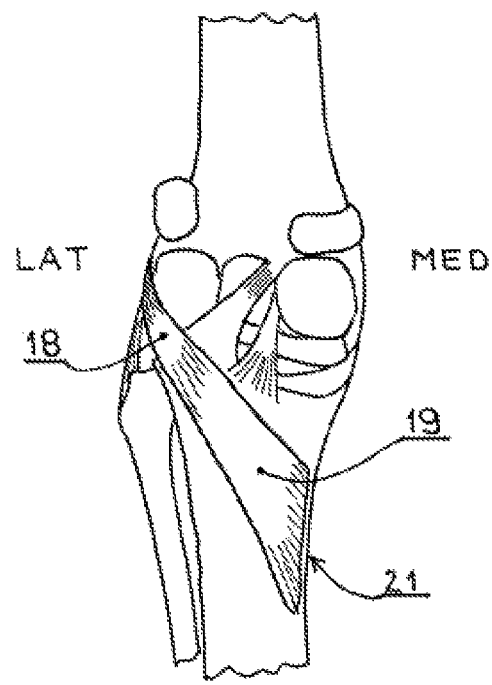
FIG. 2 is a caudal view of the anatomy of the canine stifle (left leg).

Referring to FIG. 2, the caudal view of the stifle shows the popliteal muscle 19, triangular in shape, extending from its femoral tendon 18 distally to its insertion 21 along the medial-caudal border of the tibia. From its position and attachments to the femur and the tibia, it can be seen that the popliteal muscle is an internal rotator of the tibia with respect to the femur. Whether it has any effect on flexion or extension of the stifle has been debated, but in any case, the moment generated around the flexion/extension axis is very small because the lever arm is very short. A more relevant and more detrimental consequence of the activation of the popliteal muscle is its pull on the femoral condyle in the caudal direction, which is the recognized problem in ruptured cranial cruciate ligament. This translation is commonly referred to as tibial thrust—the tibia moves cranially with respect to the femur or, said differently, the femur moves caudally with respect to the tibia.

Figure 3:
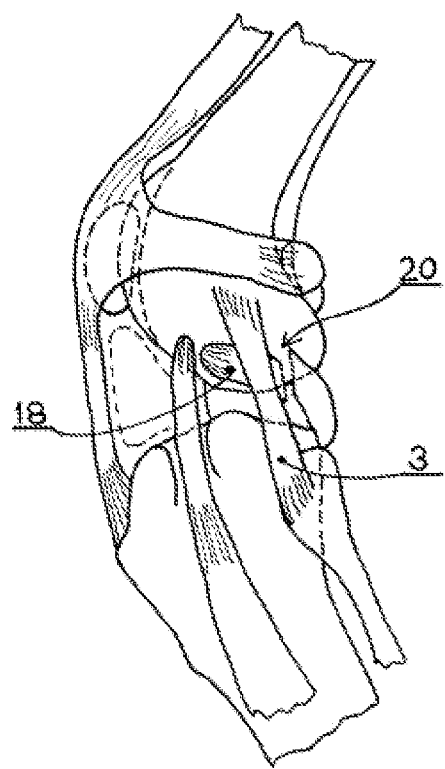
FIG. 3 is a lateral view of the canine stifle with the tendon of the popliteal muscle transected near its origin.
Figure 4:
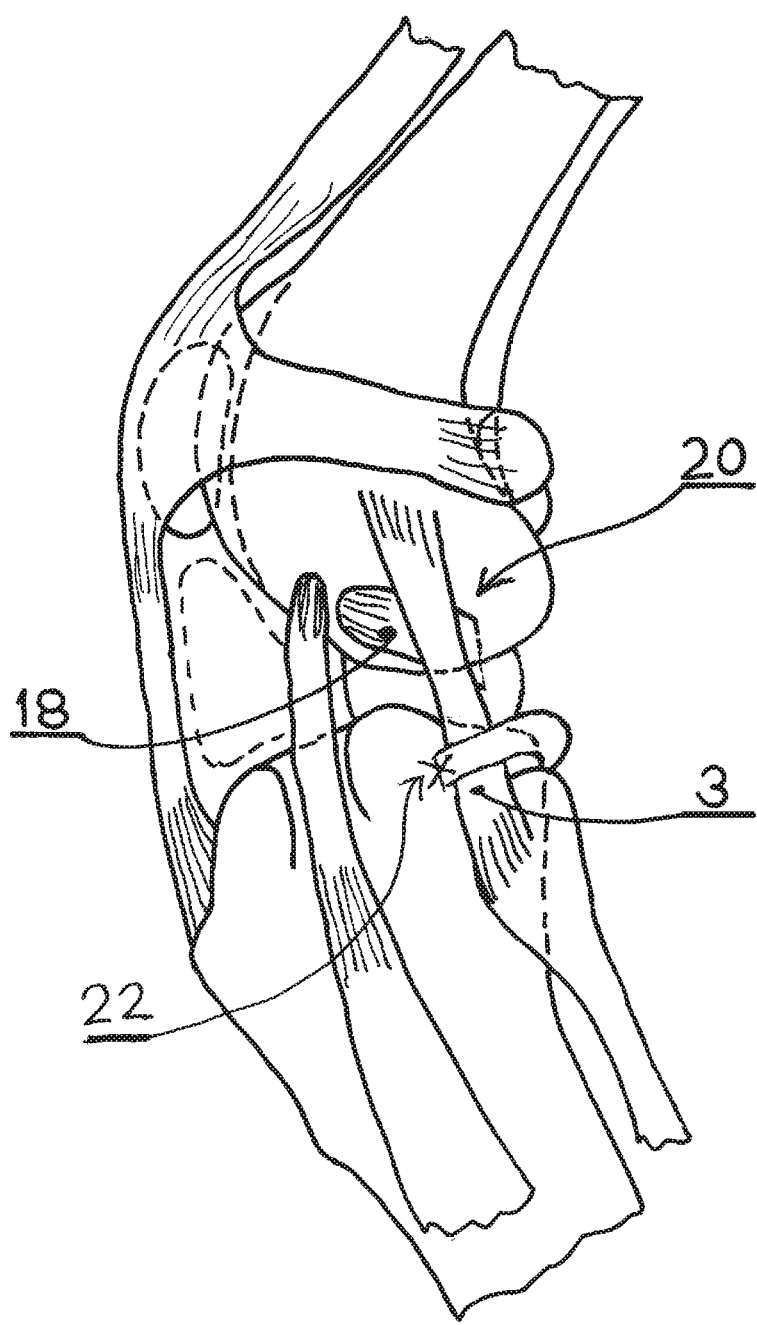
FIG. 4 is a lateral view of the canine stifle with the cut end of the popliteal muscle sutured to the tibia.

Referring to FIG. 3, as indicated above, we believe there are multiple positive effects for the stifle mechanics in cases of compromised or ruptured cruciate ligaments from transection of the tendon 18 of the popliteal muscle 19, as shown on FIG. 3 by arrow 20. In one embodiment, the methods of the invention include transecting or cutting the tendon 18 just caudally to the lateral collateral ligament 3, which is easy to identify during a standard lateral surgical approach to the stifle. To alleviate any concerns about the healing of the transected tendon 18, the methods of the invention can include a step of securing (e.g., by suturing) the distal end of the transected tendon to the tibia at, for example, the tibial attachment of the joint capsule. FIG. 4 is a diagram illustrating the suturing (with a suture 22) of a distal end of the popliteal muscle to the tibia. As noted, the popliteal muscle is cut free from its tendon as a result of transecting the tendon just caudally to a lateral collateral ligament or at an origin of the tendon of the popliteal muscle on a distal lateral side of the femoral condyle, with the origin of the tendon of the popliteal muscle located between the lateral collateral ligament and the tendon of a long digital extensor muscle.

In cases where the ruptured cruciate ligament is being replaced by an intra-articular surrogate, the transection of the tendon 18 can be effected through a minimal approach to the stifle from the lateral side. The fibular head is easy to palpate and thus also to find the location of the lateral collateral ligament that attaches to it. Tracing the collateral ligament 3 proximally along its caudal edge will bring the surgeon to the tendon 18 at the distal end of the femoral condyle.

This same, minimal approach can be used if the transection is being carried out to relieve the loading on a partially ruptured CrCL.

In cases of patellar medial luxation, the standard surgical approach is from the lateral side and can be used to identify and transect the tendon 18.

In all standard approaches for placement of the lateral extracapsular suture the tendon 18 comes in direct view and can be readily transected.

Having disclosed at least one embodiment of the present invention, variations will be understood by one of ordinary skill in the art. Such adaptations, modifications and improvements are considered part of the invention.

What is claimed is:

1. A method of treating a disordered dog stifle, the method comprising surgically transecting the tendon of the popliteal muscle just caudally to a lateral collateral ligament or at an origin of the tendon of the popliteal muscle on a distal lateral side of the femoral condyle, the origin of the tendon of the popliteal muscle located between the lateral collateral ligament and a tendon of a long digital extensor muscle, and securing a cut end of the popliteal muscle to another bone structure.

2. The method of claim 1, wherein the stifle has a partially ruptured cruciate ligament.

3. The method of claim 2, wherein the cruciate ligament is the cranial cruciate ligament.

4. The method of claim 2, wherein the cruciate ligament is the caudal cruciate ligament.

5. The method of claim 1, wherein transecting the tendon is the sole intervention performed to treat the disordered dog stifle.

6. The method of claim 1, wherein the method further comprises performing a further surgical treatment for treating the disordered dog stifle, the further surgical treatment being performed adjunctly to surgically transacting the tendon.

7. The method of claim 6, wherein the further surgical treatment comprises placing an extracapsular lateral suture.

8. The method of claim 6, wherein the further surgical treatment comprises replacing an intraarticular cranial cruciate ligament.

9. The method of claim 6, wherein the further surgical treatment comprises performing a tibial plateau leveling osteotomy (TPLO).

10. The method of claim 6 wherein the further surgical treatment comprises performing a tibial tuberosity advancement (TTA) procedure.

11. The method of claim 1, wherein the stifle has a medially luxating patella.

12. The method of claim 1, wherein the stifle has a fully ruptured cruciate ligament.

13. The method of claim 12, wherein the cruciate ligament is the cranial cruciate ligament.

14. The method of claim 12, wherein the cruciate ligament is the caudal cruciate ligament.

15. The method of claim 1, wherein securing the cut end of the popliteal muscle to the other bone structure comprises:
   securing the cut end of the popliteal muscle to the proximal tibia.

16. The method of claim 15, wherein securing the cut end of the transected popliteal muscle to the proximal tibia comprises:

suturing the cut end of the popliteal muscle to a tibial attachment of a joint capsule in order to prevent healing of the tendon and prevent re-attachment of the transected tendon to the popliteal muscle.

17. The method of claim 1, wherein surgically transecting the tendon of the popliteal muscle at the origin of the tendon of the popliteal muscle comprises surgically transecting the tendon of the popliteal muscle at the origin of the tendon of the popliteal muscle on the distal lateral side of the femoral condyle between origins of the lateral collateral ligament and the tendon of a long digital extensor muscle.

18. A method of treating a disordered dog stifle, the method comprising surgically transecting the tendon of the popliteal muscle just caudally to a lateral collateral ligament or at an origin of the tendon of the popliteal muscle on a distal lateral side of the femoral condyle, the origin of the tendon of the popliteal muscle located between the lateral collateral ligament and a tendon of a long digital extensor muscle, wherein surgically transecting the tendon of the popliteal muscle at the origin of the tendon of the popliteal muscle comprises surgically transecting the tendon of the popliteal muscle at the origin of the tendon of the popliteal muscle on the distal lateral side of the femoral condyle between origins of the lateral collateral ligament and the tendon of a long digital extensor muscle.

19. The method of claim 18, wherein the stifle has a partially ruptured cruciate ligament, and wherein the cruciate ligament is one of: the cranial cruciate ligament, or the caudal cruciate ligament.

20. The method of claim 18, wherein transecting the tendon is the sole intervention performed to treat the disordered dog stifle.

21. The method of claim 18, wherein the method further comprises performing a further surgical treatment for treating the disordered dog stifle, the further surgical treatment being performed adjunctly to surgically transacting the tendon, wherein the further surgical treatment comprises one or more of:

placing an extracapsular lateral suture,
replacing an intraarticular cranial cruciate ligament,
performing a tibial plateau leveling osteotomy (TPLO), or
performing a tibial tuberosity advancement (TTA) procedure.

22. The method of claim 18, wherein the stifle has a medially luxating patella.

23. The method of claim 18, wherein the stifle has a fully ruptured cruciate ligament that is one of: the cranial cruciate ligament, or the caudal cruciate ligament.

* * * * *